United States Patent [19]
Kortenbach et al.

[11] Patent Number: 5,846,240
[45] Date of Patent: Dec. 8, 1998

[54] CERAMIC INSULATOR FOR A BIPOLAR PUSH ROD ASSEMBLY FOR A BIPOLAR ENDOSCOPIC SURGICAL INSTRUMENT

[75] Inventors: Juergen Andrew Kortenbach, Miami Springs; Michael Sean McBrayer, Miami; Joel F. Giurtino, Miami; Saul Gottlieb, Miami, all of Fla.

[73] Assignee: Symbiosis Corporation, Miami, Fla.

[21] Appl. No.: 530,740

[22] Filed: Sep. 19, 1995

Related U.S. Application Data

[63] Continuation-in-part of Ser. No. 354,992, Dec. 13, 1994, and Ser. No. 284,793, Aug. 2, 1994, Pat. No. 5,569,243.

[51] Int. Cl.⁶ .................................................. A61B 17/38
[52] U.S. Cl. ............................... 606/48; 606/50; 606/174
[58] Field of Search ........................... 606/45, 48–52, 606/46–47, 174

[56] References Cited

U.S. PATENT DOCUMENTS

| | | | |
|---|---|---|---|
| 3,651,811 | 3/1972 | Hildebrandt et al. | |
| 3,920,021 | 11/1975 | Hiltebrandt | 128/303.17 |
| 4,003,380 | 1/1977 | Wien | 128/303.17 |
| 4,418,692 | 12/1983 | Guay | |
| 5,007,908 | 4/1991 | Rydell | |
| 5,035,696 | 7/1991 | Rydell | 606/47 |
| 5,078,717 | 1/1992 | Parins et al. | 606/48 |
| 5,085,659 | 2/1992 | Rydell | 606/47 |
| 5,258,006 | 11/1993 | Rydell et al. | 606/205 |
| 5,324,289 | 6/1994 | Eggers | |
| 5,330,471 | 7/1994 | Eggers | 606/48 |
| 5,342,381 | 8/1994 | Tidemand | 606/174 |
| 5,352,223 | 10/1994 | McBrayer et al. | 606/51 |
| 5,391,166 | 2/1995 | Eggers | 606/48 |
| 5,514,134 | 5/1996 | Rydell et al. | 606/48 X |

*Primary Examiner*—Robert L. Nasser
*Assistant Examiner*—Ryan Carter
*Attorney, Agent, or Firm*—Finnegan, Henderson, Farabow, Garrett & Dunner, L.L.P.

[57] ABSTRACT

A bipolar push rod assembly is disclosed in conjunction with an endoscopic bipolar cautery scissors instrument. The push rod assembly has two conductive push rods which are substantially covered and insulated from each other by a double lumen flexible sheath. The proximal ends of the push rods are stabilized by an overmolded plastic collar and the distal ends of the push rods are stabilized by a ceramic insulator. The plastic collar is provided with a snap retainer for coupling it to a plastic plug retainer having a pair of spaced apart passages. A pair of female plug adapters are press fit onto the proximal ends of the push rods and are maintained in place by the plug retainer with each adaptor residing in a respective one of the passages. The distal ends of the push rods are swaged approximately 90° in opposite directions. A ceramic insulator is disclosed as a one-piece unit into which the distal ends of the push rods are inserted. Another ceramic insulator is disclosed as a two-piece member which fits around the distal ends of the push rods. A double lumen sealing gasket which interrupts the double lumen sheath is also disclosed.

20 Claims, 6 Drawing Sheets

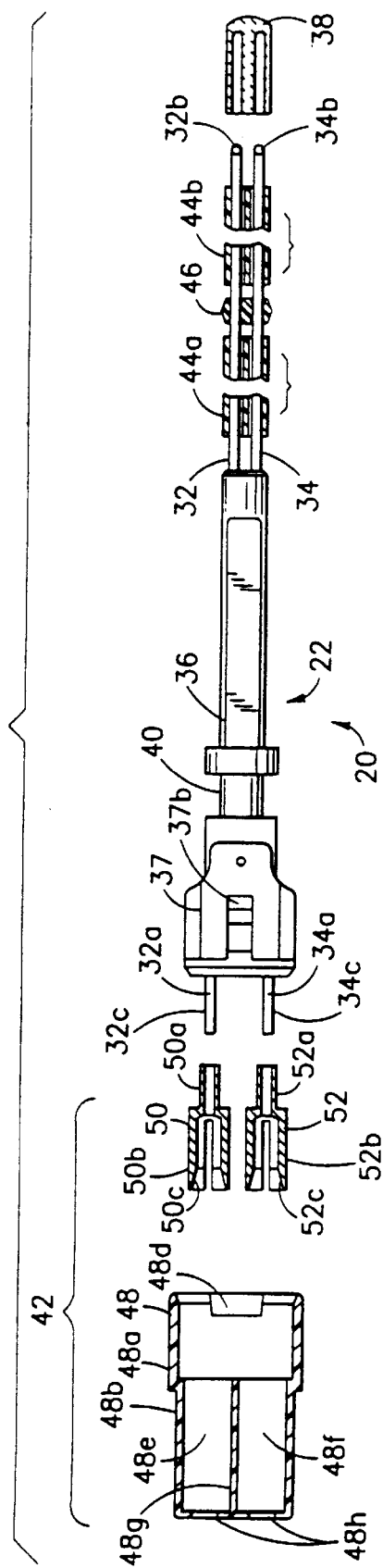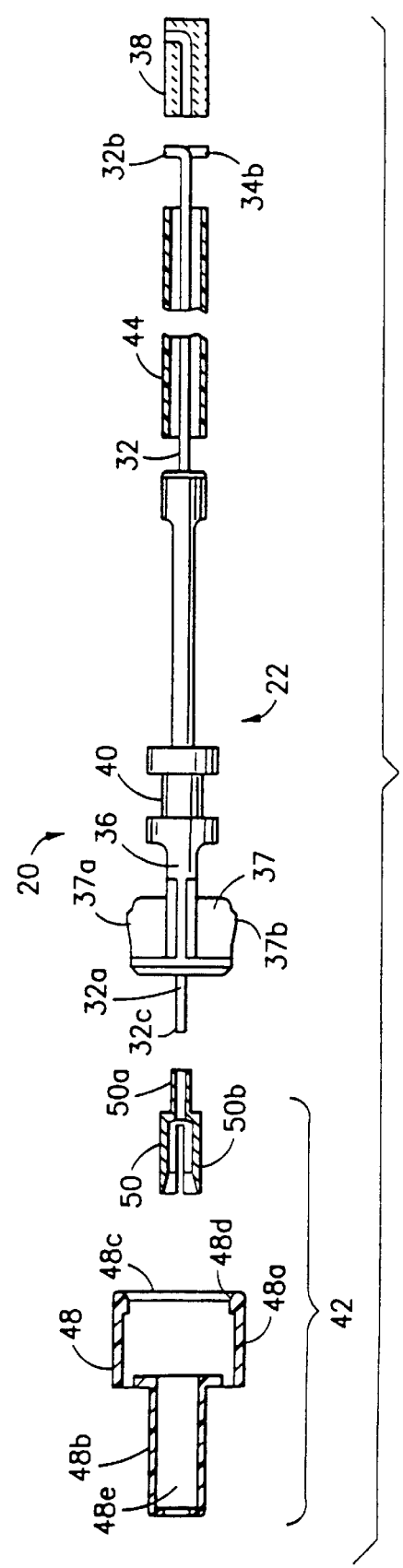

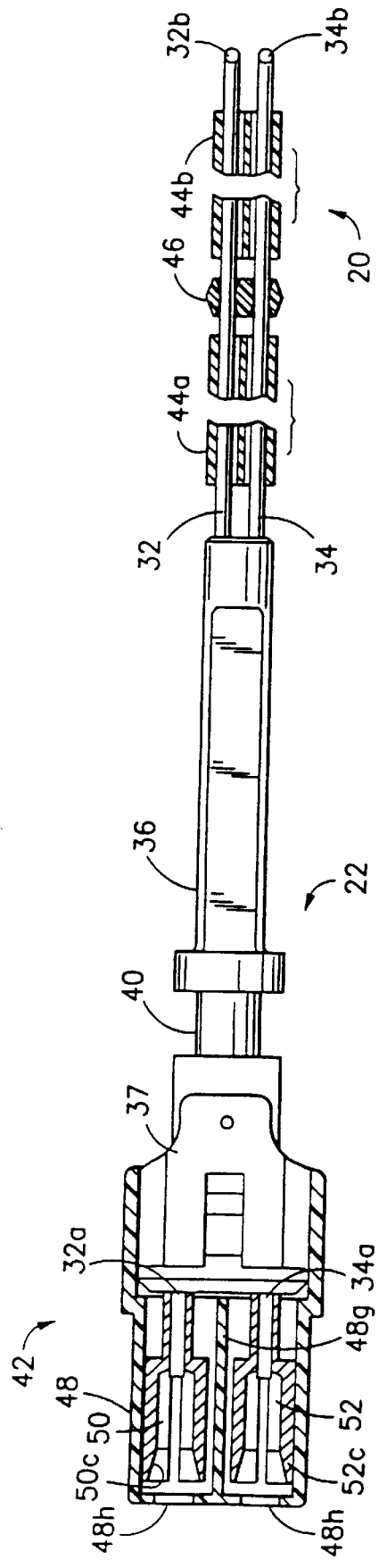
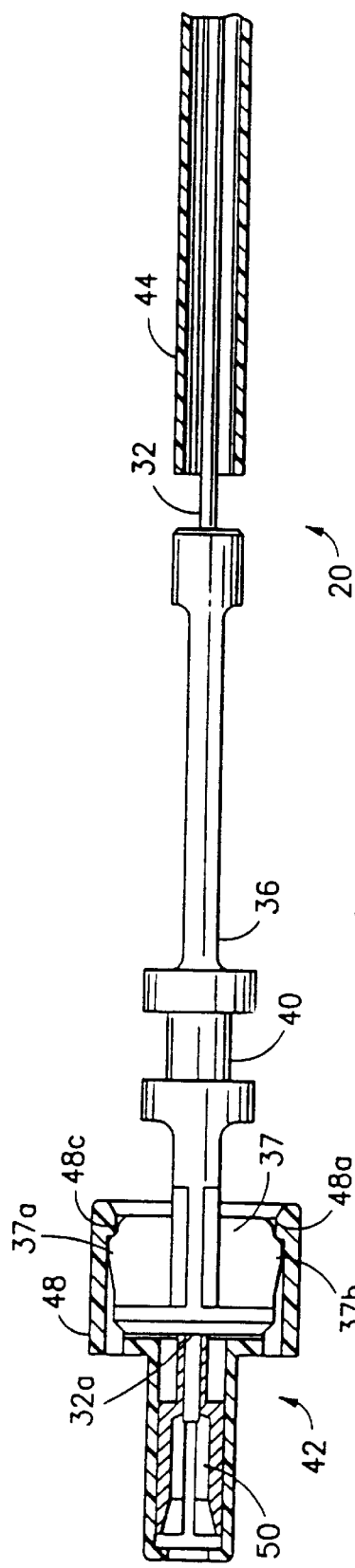

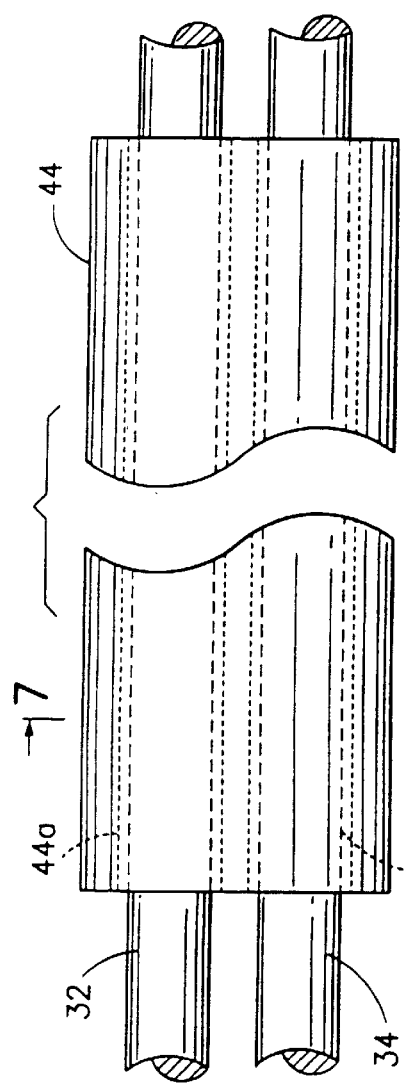
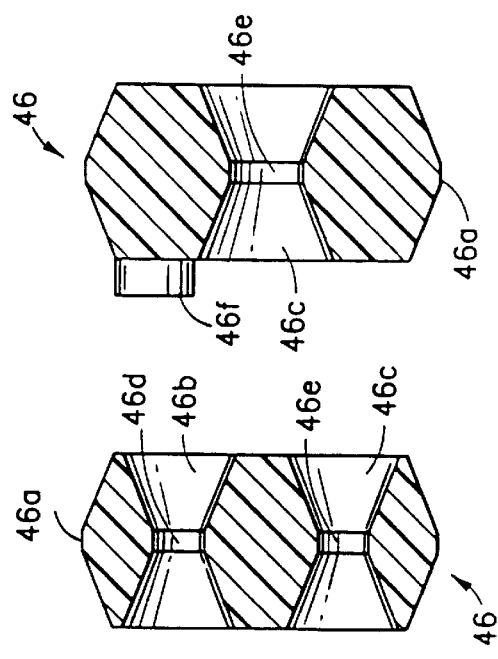
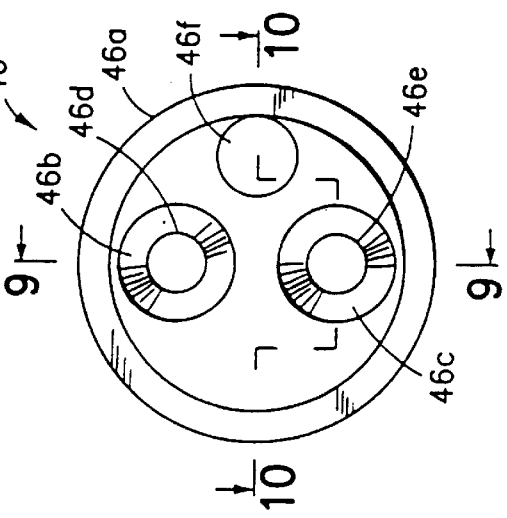
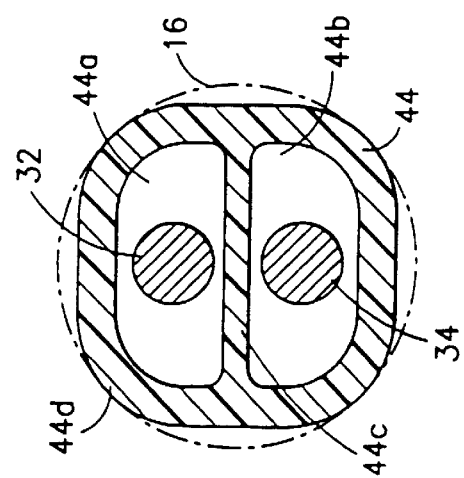
FIG. 6
FIG. 7
FIG. 8
FIG. 9
FIG. 10

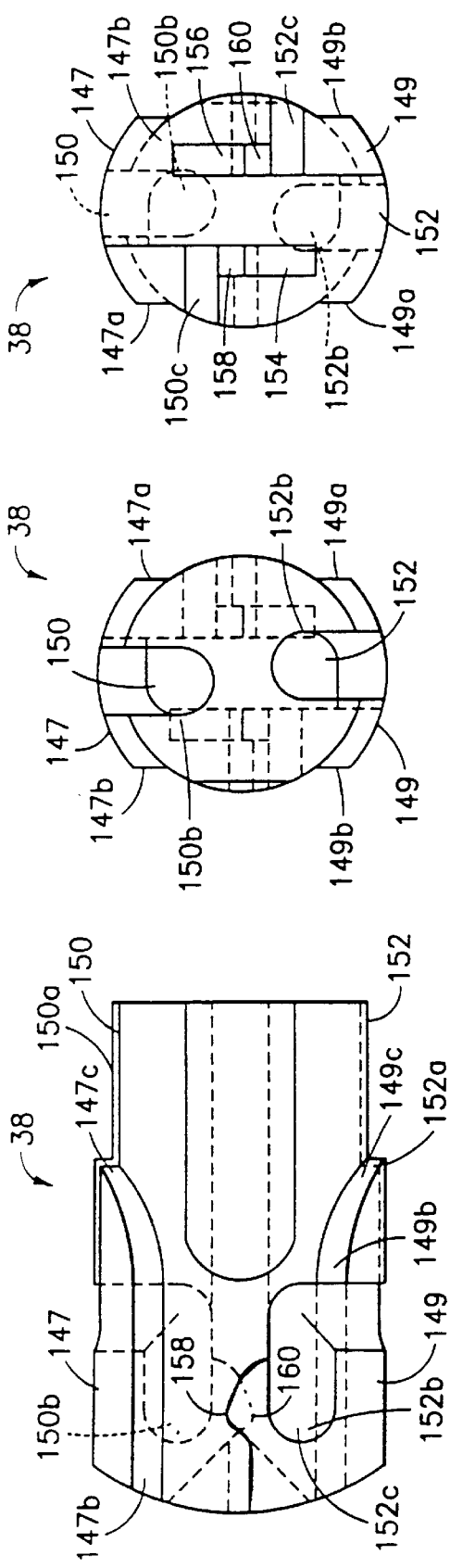
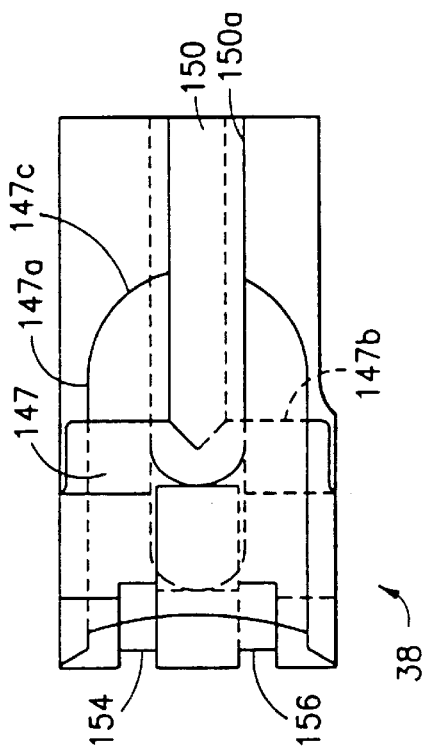
FIG. 11
FIG. 12
FIG. 13
FIG. 14

CERAMIC INSULATOR FOR A BIPOLAR PUSH ROD ASSEMBLY FOR A BIPOLAR ENDOSCOPIC SURGICAL INSTRUMENT

This application is a continuation-in-part of Ser. No. 08/354,992 filed Dec. 13, 1994, which is pending. This application is also related to co-owned application Ser. No. 08/284,793 filed Aug. 2, 1994, now the U.S. Pat. No. 5,569,243, the complete disclosure of which is hereby incorporated herein by reference.

BACKGROUND OF THE INVENTION

1. Field of the Invention

The present invention relates generally to endoscopic surgical instruments. More particularly, the invention relates to a ceramic insulator for a bipolar push rod assembly for an endoscopic surgical instrument having bipolar endoscopic cautery capability.

2. State of the Art

Endoscopic surgery is widely practiced throughout the world today and its acceptance is growing rapidly. In general, endoscopic/laparoscopic surgery involves one or more incisions made by trocars where trocar tubes are left in place so that endoscopic surgical tools may be inserted through the tubes. A camera, magnifying lens, or other optical instrument is often inserted through one trocar tube, while a cutter, dissector, or other surgical instrument is inserted through the same or another trocar tube for purposes of manipulating and/or cutting the internal organ. Sometimes it is desirable to have several trocar tubes in place at once in order to receive several surgical instruments. In this manner, organ or tissue may be grasped with one surgical instrument, and simultaneously may be cut with another surgical instrument; all under view of the surgeon via the optical instrument in place in the trocar tube.

Various types of endoscopic surgical instruments are known in the art. These instruments generally comprise a slender tube containing a push rod which is axially movable within the tube by means of a handle or trigger-like actuating means. An end effector is provided at the distal end of the tube and is coupled to the push rod by means of a clevis so that axial movement of the push rod is translated to rotational or pivotal movement of the end effector. End effectors may take the form of scissors, grippers, cutting jaws, forceps, and the like.

Modern endoscopic procedures often involve the use of electrocautery, as the control of bleeding by coagulation during surgery is critical both in terms of limiting loss of blood and in permitting a clear viewing of the surgical site. As used herein, cautery, electrocautery, and coagulation are used interchangeably. Several types of electrocautery devices for use in endoscopic surgery are described in the prior art. Monopolar electrosurgical instruments employ the instrument as an electrode, with a large electrode plate beneath and in contact with the patient serving as the second electrode. High frequency voltage spikes are passed through the instrument to the electrode (i.e., end effector) of the endoscopic instrument to cause an arcing between the instrument and the proximate tissue of the patient. The current thereby generated continues through the patient to the large electrode plate beneath the patient. Monopolar cautery has the disadvantage that the current flows completely through the patient. Because control of the current path through the body is not possible, damage can occur to tissue both near and at some distance from the surgical site. In addition, it is has been observed that monopolar cautery can result in excessive tissue damage due to the arcing between the end effector and the tissue.

In order to overcome the problems associated with monopolar cautery instruments, bipolar instruments have been introduced. In bipolar electrosurgical instruments, two electrodes which are closely spaced together are utilized to contact the tissue. Typically, one end effector acts as the first electrode, and the other end effector acts as the second electrode, with the end effectors being electrically isolated from each other and each having a separate current path back through to the handle of the instrument. Thus, in a bipolar instrument, the current flow is from one end effector electrode, through the tissue to be cauterized, to the other end effector electrode.

Various endoscopic instruments with cautery capability are known in the art. U.S. Pat. No. 4,418,692 to Guay, for example, discloses a device for use in laparoscopic tubal cauterization for blocking the Fallopian tubes of a patient. The device comprises a substantially tubular body member having a spring-biased piston slidably mounted therein. A pair of electrodes (either monopolar or bipolar) are disposed to grasp living tissue when the piston is in a first position biased by the spring and to release the tissue when a button is pressed which moves the piston into a second position. The device includes a circuit breaker which interrupts current flowing to the electrodes when the piston is in the second position. When the electrodes grasp the tissue, however, current is supplied to the entire surface of the electrode, that is, both the grasping surface and the outer non-grasping surface.

Another electrosurgical instrument for use in combination with an endoscope is disclosed in U.S. Pat. No. 5,007,908 to Rydell for "Electrosurgical Instrument Having Needle Cutting Electrode and Spot-Coag Electrode". Rydell's device includes an elongated flexible tubular member with a plurality of lumens. The distal end of the tubular member is provided with a bullet shaped ceramic tip covered with a conductive layer and having an opening coupled to a first one of the lumens. The conductive layer is coupled to a conductor which extends through a second one of the lumens to an electrical source. A second conductor, also coupled to the electrical source is slidable through the first lumen by a plunger. The two electrodes form a bipolar pair. In a second embodiment, the conductive layer on the ceramic tip is split by an insulating gap and both halves of the tip form a bipolar pair of electrodes. As with the Guay device, above, substantially the entire distal surface of Rydell's device serves as an electrode when energized.

Several hemostatic bipolar electrosurgical scissors have also been described. U.S. Pat. No. 3,651,811 to Hildebrandt describes a bipolar electrosurgical scissors having opposing cutting blades forming active electrodes. The described scissors enables a surgeon to sequentially coagulate the blood vessels contained in the tissue and then to mechanically sever the tissue with the scissor blades. In particular, with the described bipolar electrosurgical scissors, the surgeon must first grasp the tissue with the scissor blades, energize the electrodes to cause hemostasis, de-energize the electrodes, and then close the scissor blades to sever the tissue mechanically. The scissors are then repositioned for another cut accomplished in the same manner. With the bipolar electrosurgical scissors of Hildebrandt, the surgeon cannot maintain the electrodes in a continuously energized state because the power supply would be shorted out and/or the blades damaged if the blades are permitted to contact each other while energized.

The disadvantages of the bipolar scissors of Hildebrandt are overcome by the disclosure in U.S. Pat. Nos. 5,324,289 and 5,330,471 to Eggers. In its preferred embodiment, the bipolar electrosurgical scissors of Eggers comprise a pair of metal scissor blades which are provided with an electrically insulating material interposed between the shearing surfaces of the blades so that when the scissor blades are closed, the metal of one blade never touches the metal of the other blade; i.e., the insulating material provides the cutting edge and the shearing surface. With the arrangement provided by Eggers, a cautery current will pass from the top back edge of the bottom metal blade through the tissue which is to be cut and to the bottom back edge of the top metal blade directly in advance of the cutting action. As the scissors are gradually closed, the hemostasis preferentially occurs at a location just in advance of the cutting point which itself moves distally along the insulated cutting edges of the blades in order to sever the hemostatically heated tissue. With this arrangement, the scissors may be maintained in a continuously energized state while performing the cutting. The Eggers patent describes various alternative embodiments of the bipolar scissors, including the use of metal blades with only one blade being insulated on its shearing surface, and the use of insulating blades with back surfaces coated with metal.

In all of the bipolar instruments, and particularly in double acting instruments such as scissors, safe and effective delivery of the cautery current to the end effectors is always a difficult engineering problem. In particular, it is difficult to deliver a bipolar current source within the limited space in which endoscopic surgery is performed. It is necessary to assure that the conductors delivering the current are well insulated from each other, that they are easily connected to the end effectors, and that they are easily connected to a standard source of bipolar cautery current. Both Rydell et al. (U.S. Pat. No. 5,258,006) and Eggers (U.S. Pat. No. 5,330,471) have proposed bipolar push rod arrangements. Eggers has proposed a bifurcated cylindrical push rod in which two halves of the push rod are conductive and which are both covered with an insulating material. Rydell et al. has proposed a pair of conductive leads which extend through a double lumen silastic or polyurethane push rod. Neither of the bipolar push rod arrangements is easy to implement, and neither has been commercially successful. Moreover, the arrangement taught by Rydell et al. cannot be used with pivoting double acting end effectors as is required in the art of interest.

SUMMARY OF THE INVENTION

It is therefore an object of the invention to provide a bipolar push rod assembly for a bipolar endoscopic instrument.

It is another object of the invention to provide a bipolar push rod assembly which is easy to manufacture.

It is also an object of the invention to provide a bipolar push rod assembly which is well insulated to prevent a short circuit.

It is another object of the invention to provide a bipolar push rod assembly which is easily coupled to double acting end effectors.

It is still another object of the invention to provide a bipolar push rod assembly which is easily coupled to a standard source of cautery current.

In accord with the objects of the invention, a bipolar push rod assembly is disclosed in conjunction with an endoscopic bipolar cautery scissors instrument which is substantially as is described in copending application U.S. Ser. No. 08/284,793. The push rod assembly, according to the invention, has two conductive push rods which are stabilized relative to each other at their proximal and distal ends and which are otherwise substantially covered by a double lumen flexible sheath. The proximal ends of the push rods are stabilized by an overmolded plastic collar, and the distal ends of the push rods are stabilized by a ceramic insulator.

In accord with one aspect of the invention, the proximal ends of the push rods are swaged so that they exit a plastic collar spaced apart from each other approximately the same distance as the pins of a conventional cautery connector plug. The plastic collar is provided with a snap retainer for coupling it to a plastic plug retainer having a pair of spaced apart passages. A pair of female plug adapters are press fit onto the proximal ends of the push rods and are maintained in place by the plug retainer with each adaptor residing in a respective one of the passages. The distal ends of the push rods are swaged approximately 90° in opposite directions.

In accord with another aspect of the invention, the ceramic insulator may either be a one-piece unit into which the distal ends of the push rods are inserted, or a two-piece member which fits around the distal ends of the push rods. In either case, the ceramic insulator provides longitudinal channels for the push rods with substantially right angle bends at the distal ends of the channels. In addition, intersecting the substantially right angle bends are distal slots which can accommodate links which couple the push rods to the end effectors.

The push rod assembly according to the invention extends through the hollow tube of the bipolar instrument with the swaged distal ends of the push rods being coupled to the end effectors by links and the plastic collar being coupled to the movable lever of the handle. According to a preferred embodiment of the invention, a double lumen sealing gasket is located between the plastic collar and the ceramic insulator. Preferably, the double lumen sheath is bifurcated and the sealing gasket is located between a proximal double lumen sheath and a distal double lumen sheath. The sealing gasket fills the space between the push rod assembly and the interior of the hollow tube to prevent fluids from escaping the surgical site through the hollow tube.

Additional objects and advantages of the invention will become apparent to those skilled in the art upon reference to the detailed description taken in conjunction with the provided figures.

BRIEF DESCRIPTION OF THE DRAWINGS

FIG. 1 is a broken side elevation view in partial section of an endoscopic bipolar scissors instrument incorporating the push rod assembly according to the invention;

FIG. 1a is an enlarged broken exploded top view in partial section of the distal end of the instrument of FIG. 1;

FIG. 1b is a cross sectional view taken along line 1B—1B of FIG. 1a;

FIG. 2 is an exploded broken partially transparent side elevation view of the push rod assembly according to the invention;

FIG. 3 is an exploded broken partially transparent top view of the push rod assembly according to the invention;

FIG. 4 is an enlarged broken partially transparent side elevation view of the proximal end of the push rod assembly;

FIG. 5 is an enlarged broken partially transparent top view of the proximal end of the push rod assembly;

FIG. 6 is a broken side elevation view of a double lumen sheath according to the invention;

FIG. 7 is a cross section taken along line 7—7 of FIG. 6;

FIG. 8 is a plan view of a double lumen gasket according to the invention;

FIG. 9 is a cross section taken along line 9—9 of FIG. 8;

FIG. 10 is a sectional view taken along line 10—10 of FIG. 8;

FIG. 11 is a side elevation view of a one-piece ceramic insulator according to the invention;

FIG. 12 is a proximal end view of the insulator of FIG. 11;

FIG. 13 is a distal end view of the insulator of FIG. 11;

FIG. 14 is a top view of the insulator of FIG. 11;

DETAILED DESCRIPTION OF THE PREFERRED EMBODIMENTS

Figures 1, 1A, 1B:
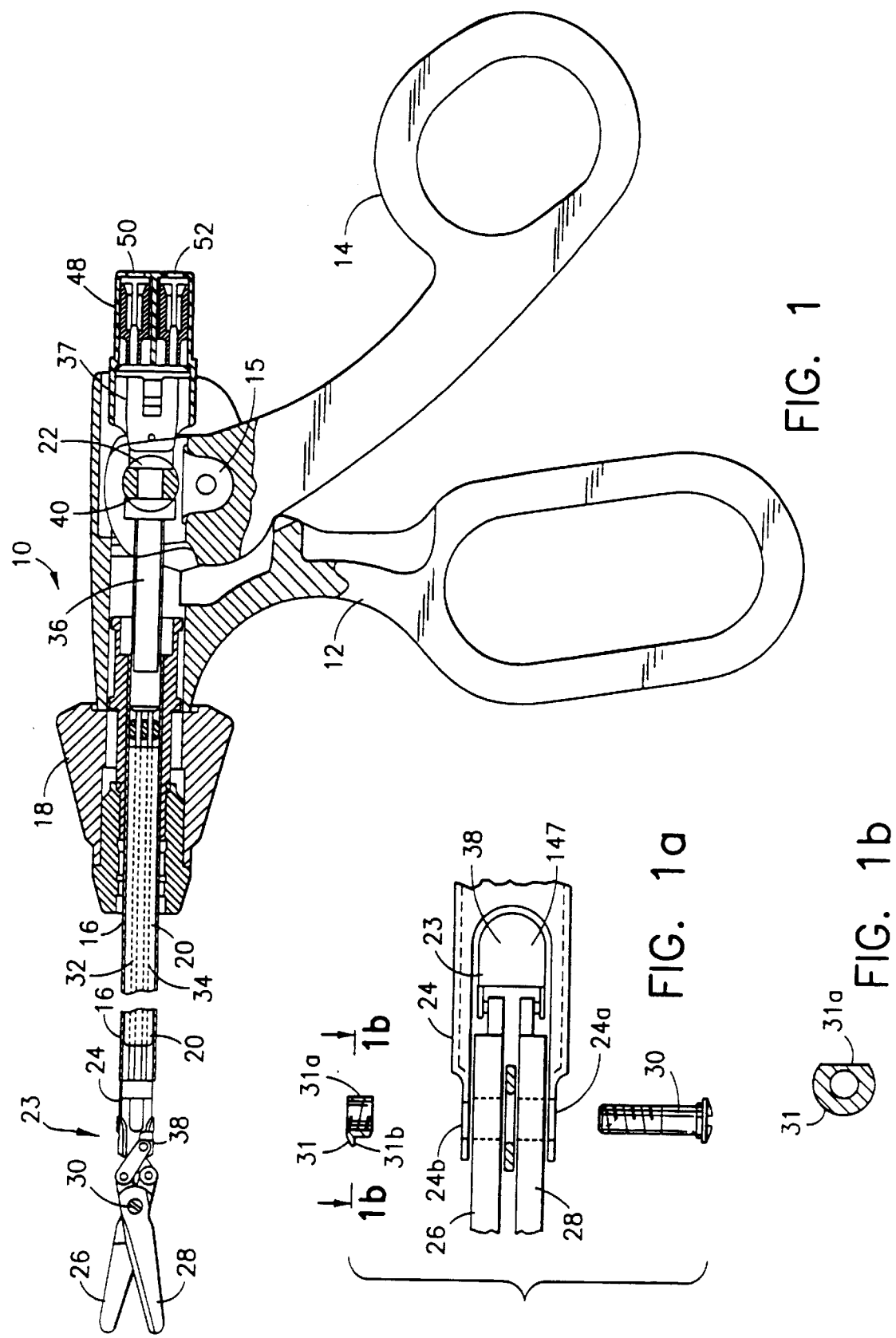

Turning now to FIG. 1, a bipolar endoscopic instrument 10 includes a proximal handle 12 with a manual lever actuator 14 pivotally coupled to the handle by a pivot pin 15. A hollow stainless steel tube 16 is rotatably coupled to the handle 12 and is preferably rotatable about its longitudinal axis relative to the handle 12 through the use of a ferrule 18 such as described in detail in previously incorporated copending application Ser. No. 08/284,793. A push rod assembly 20 extends through the hollow tube 16 and is coupled at its proximal end 22 to the manual lever actuator 14 as described in more detail in copending application Ser. No. 08/284,793. The distal end of the tube 16 has an integral clevis 24 within which a pair of end effectors (in this case scissor blades) 26, 28 are mounted on an axle screw 30. The distal end 23 of the push rod assembly 20 is coupled to the scissor blades 26, 28 so that reciprocal movement of the push rod assembly 20 relative to the tube 16 opens and closes the scissor blades 26, 28. It will be appreciated that the reciprocal movement of the push rod assembly 20 relative to the tube 16 is effected by movement of the manual lever actuator 14 relative to the handle 12. According to a preferred aspect of the instrument 10, as illustrated in FIGS. 1a and 1b, the axle screw 30 is secured in the clevis 24 by a nut 31 which has a flat side 31a and a D-shaped flange 31b. The clevis 24 is provided with a round hole 24a for receiving the screw 30 and a D-shaped hole 24b for receiving the nut 31. The nut 31 facilitates the tightening of the screw 30. When the nut 31 is inserted in the hole 24b, the flat side 31a of the nut 31 engages the flat side of the D-shaped hole 24b so that the nut is keyed to the hole and is prevented from rotating. The flange 31b prevents the nut from passing through the hole 24b. The screw 30 can then be tightened a desired amount without holding the nut 31 while tightening.

Turning now to FIGS. 2 and 3, the push rod assembly 20, according to the invention, includes a pair of stainless steel rods 32, 34 having proximal ends 32a, 34a, and distal ends 32b, 34b. The proximal ends 32a, 34a of the push rods have divergent bends (not shown) which cause the rods to terminate in parallel proximal pins 32c, 34c. The proximal ends of the rods, with the exception of the pins 32c, 34c, are provided with an over-molded proximal collar 36. The proximal collar 36 has an increased diameter proximal portion 37 which accommodates the proximal bent portions of the rods, and a radial groove 40 which is located distally of the increased diameter portion and which is used for coupling the lever actuator 14.

According to one aspect of the invention, the proximal end 22 of the push rod assembly 20 is provided with a snap-together female cautery connector 42, described in detail below with reference to FIGS. 4 and 5. According to another aspect of the invention, a double lumen insulating sheath 44, described in more detail below with reference to FIGS. 6 and 7, covers substantially the entire length of the rods 32, 34 between the proximal collar 36 and the distal ends 32b, 34b. According to a further aspect of the invention, a double lumen sealing gasket 46, described in more detail below with reference to FIGS. 8–10, is provided on the rods 32, 34, between the proximal collar 36 and the distal insulator 38. According to still another aspect of the invention, the distal ends 32b, 34b of the push rods are swaged approximately 90° in opposite directions as shown in FIG. 3, and are captured in a distal ceramic insulator 38 which is described in detail below with reference to FIGS. 11–17.

Referring now to FIGS. 2 through 5, the female cautery connector 42 includes a plug retainer 48 and a pair of female plug adapters 50, 52. The plug retainer 48 has a substantially cylindrical distal portion 48a and a substantially rectilinear proximal portion 48b. The distal portion 48a has a pair of interior proximally ramped protrusions 48c, 48d and the proximal portion 48b has two substantially parallel passages 48e, 48f. Each plug adaptor 50, 52 is a substantially cylindrical conductive metal member having a smaller diameter distal portion 50a, 52a and a larger diameter proximal portion 50b, 52b. The distal portions 50a, 52a are dimensioned to fit snugly over the respective proximal pin ends 32c, 34c of the rods 32, 34, and the proximal portions 50b, 52b are dimensioned to fit snugly in respective passages 48e, 48f of the plug retainer 48. The increased diameter proximal portion 37 of the collar 36 is substantially frustroconical (i.e., ramped) and has a pair of distally ramped outer protrusions 37a, 37b. The cautery connector 42 is assembled by fitting the distal portions 50a, 52a of the female plug adapters 50, 52 onto the respective proximal ends 32a, 34a of the rods 32, 34, and then snap-fitting the plug retainer 48 onto the proximal portion 37 of the collar 36. As seen best in FIGS. 4 and 5, the distal portion 48a of the plug retainer 48 fits over the proximal portion 37 of the collar 36 with the ramped protrusions 48c, 48d engaging the protrusions 37a and 37b of the proximal portion 37 of the collar 36. The proximal portions 50b, 52b of the plug adapters 50, 52 are captured in the passages 48e, 48f of the plug retainer 48. When assembled, the cautery connector 42 receives a standard male cautery plug (not shown).

Turning now to FIGS. 6 and 7, the double lumen insulating sheath 44, according to the invention, has a first lumen 44a and a second lumen 44b, which are defined by a dividing wall 44c, and an outer wall 44d. The first lumen 44a and second lumen 44b are substantially identical in size and shape, and are large enough in cross-sectional size to accommodate respective rods 32, 34. According to a presently preferred embodiment, the sheath 44 has an oblate cross section as seen best in FIG. 7 and the lumens 44a, 44b have a substantially D-shaped cross section. The sheath is preferably made of Himont Profax 6523 polypropylene and has an outer wall thickness of approximately 0.020 inches. When used with the instrument 10 shown in FIG. 1, the external diameter of the sheath is less than 0.169 inches and the interior diameter of the tube 16 is 0.170 inches. When so dimensioned, the lumens 44a, 44b are each approximately 0.050 inches by approximately 0.112 inches in cross section.

While not essential to the electrical or mechanical performance of the push rod assembly, it is preferable to provide a sealing gasket to seal the annular space between the push rod assembly and the tube of the endoscopic instrument as mentioned above. Turning now to FIGS. 8–10, a sealing gasket 46, according to the invention, is preferably formed of injection molded Santoprene 281-64 thermoplastic rubber having a Durometer of 64. The gasket 46 is preferably tapered proximally and distally to define a waist portion 46a which has a diameter larger than the inner diameter of the tube 16 of the instrument 10 (FIG. 1). For example, when used with a tube having an inner diameter of 0.170 inches, the diameter of the waist portion 46a is preferably approximately 0.177 inches. The gasket 46 is provided with two lumens 46b, 46c which are flared proximally and distally to define respective inner waists 46d, 46e having diameters which are preferably smaller than the outer diameters of the rods 32, 32 (FIGS. 1–5). For example, the instrument 10 described above has rods 32, 34 which each have a diameter of approximately 0.040 inches. When used with rods so dimensioned, the waists 46d, 46e each have a diameter of approximately 0.033 inches. As so dimensioned, the overall width of the gasket 46 is approximately 0.090 inches. As mentioned above, the gasket may be placed between the sleeve 44 and the proximal collar 36 or between the sleeve 44 and the distal insulator 38. As mentioned above, the presently preferred method of making the gasket 46 is by injection molding and FIGS. 8 and 10 show the approximate gate location where a portion 46f of the molded material protrudes from the gate of the mold. In accord with the exemplary dimensions given above, a gate protrusion of approximately 0.020 inches is permissible. As mentioned above, the sealing gasket 46 may be placed almost anywhere between the proximal collar 36 and the distal ends 32b, 34b of the push rods. According to a presently preferred embodiment, however, as shown in FIGS. 2 and 4, the sheath 44 is bifurcated into a proximal portion 44a and a distal portion 44b, and the sealing gasket 46 is located between these portions 44a, 44b.

Referring now to FIGS. 11 through 14, the presently preferred embodiment of the distal insulator 38 comprises a single piece ceramic member. The insulator 38 is substantially circular in cross section except for upper and lower projections 147, 149. These projections engage the space between arms of the clevis 24 (FIG. 1) and prevent the insulator 38 from rotating in the clevis during reciprocation 24 and from passing beyond the proximal end of the clevis as described in copending application Ser. No. 08/354,992. Consequently, the projections each have a pair of substantially parallel edges 147a, 147b, 149a, 149b and a rounded proximal edge 147c, 149c. The insulator 38 has a pair of push rod receiving channels 150, 152 for fixedly receiving the push rods 32, 34 (FIGS. 1–5) respectively. The channels have portions 150a, 152a which are radially open to the surface of the insulator 38 from the proximal end thereof to a point approximately half way under the projections 147, 149. The channels 150, 152 terminate under the projections 147, 149 with a right angle bend 150b, 152b. A radial opening 150c, 152c extends proximally along each side of the insulator from the right angle bend 150b, 152b to a point contiguous with the radially open part 150a, 152a of the channels 150, 152. The radial openings 150c, 152c are each substantially orthogonal to the radially open parts 150a, 152a. The distal end of the insulator 38 has a pair of ramped slot openings 154, 156 which terminate at their proximal ends with curved grooves 158, 160. The slot openings and grooves are provided to accommodate the ends of links as described in copending application Ser. No. 08/354,992 for coupling the distal ends 32b, 34b (FIG. 3) of the push rods 32, 34 to scissor blades (FIG. 1). The insulator 38 is easily attached to the distal ends of the push rods by pressing the push rods into the radially open parts 150a, 152a of the channels 150, 152 so that the bent ends 32b, 34b of the push rods enter the radial openings 150c, 152c. The push rods and/or the insulator 38 are pushed towards each other so that the bent ends of the push rods fixedly abut the right angle bends 150b, 152b in the channels 150, 152, at which location the links are coupled to the push rods. As a result of the fixed connection between the push rods and distal insulator 38, reciprocation of the push rods produces a reciprocation of the insulator.

Figure 16:
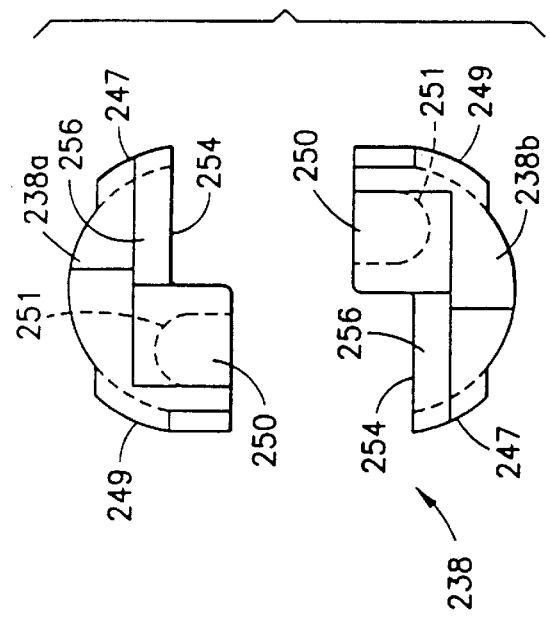
FIG. 16 is an exploded distal end view of the insulator of FIG. 15.
Figure 15:
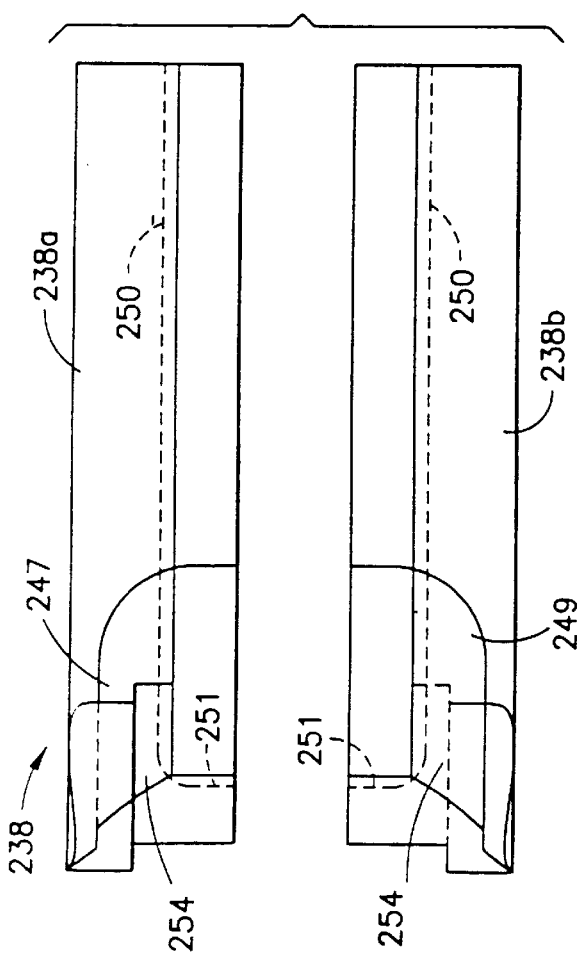
FIG. 15 is an exploded top view of a two-piece ceramic insulator according to the invention.
Figure 17:
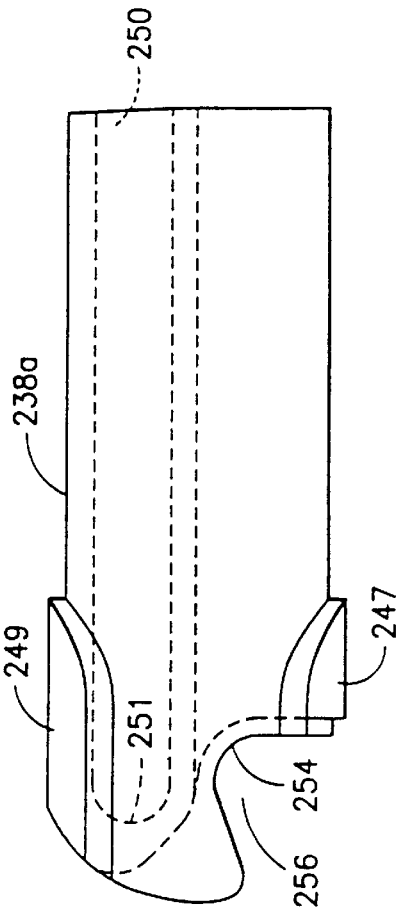
FIG. 17 is a side elevation view of one piece of the two-piece insulator of FIG. 15.

Referring now to FIGS. 15 through 17, an alternate embodiment of a distal insulator 238 is constructed of two substantially identical ceramic pieces 238a, 238b. Each piece is substantially semi-circular in cross section except for distal radial projections 247, 249. When the pieces are assembled as suggested in FIGS. 15 and 16, these projections form the same kind of projection as the projections 147, 149 described above. In addition, each of the pieces 238a, 238b has a push rod receiving channel 250 for receiving a respective one of the push rods 32, 34 (FIGS. 1–5). The channel 250 terminates adjacent to the projection 249 with a right angle bend 251. The distal end of each piece 238a, 238b has a slot opening 254 which is substantially diametrically opposite to the right angle bend 251, and a radial opening 256 adjacent to the slot opening 251 interrupts the projection 247. The slot openings and radial openings are provided to accommodate the ends of links as described in copending application Ser. No. 08/354,992 for coupling the distal ends 32b, 34b (FIG. 3) of the push rods 32, 34 to scissor blades (FIG. 1). The insulator 238 is easily attached to the distal ends of the push rods by pressing each push rod into the channel 250 of a respective piece 238a, 238b so that the bent ends 32b, 34b of the push rods abut the right angle bend 251. The two pieces are pressed together as suggested in FIGS. 15 and 16 and the distal end of each push rod enter the radial opening 256 of a respective piece.

There have been described and illustrated herein several embodiments of a push rod assembly and a bipolar endoscopic surgical instrument incorporating them. While particular embodiments of the invention have been described, it is not intended that the invention be limited thereto, as it is intended that the invention be as broad in scope as the art will allow and that the specification be read likewise. Thus, while particular conductive and non-conductive materials have been disclosed, it will be appreciated that other materials could be utilized. Also, while specific dimensions have been disclosed, it will be recognized that different dimensions could be used with similar results obtained. In addition, while the push rod assembly has been shown in conjunction with a bipolar scissors instrument, it will be appreciated that the push rod assembly can be used with any double-acting bipolar surgical instrument. Further, while the sealing gasket has been shown as interrupting the double-lumen tubing, it will be appreciated that the gasket could be located proximally or distally of the tubing as desired. It will therefore be appreciated by those skilled in the art that yet other modifications could be made to the provided invention without deviating from its spirit and scope as so claimed.

It is claimed:

1. An insulator for use in combination with a bipolar push rod assembly in a bipolar endoscopic instrument where the bipolar push rod assembly has a pair of conductive rods with each of the rods having a distal end which is swaged approximately 90°, said insulator comprising:

a substantially cylindrical reciprocating member within said push rod assembly having i) a pair of longitudinal channels for receiving said pair of conductive rods, each of said longitudinal channels terminating in an approximately 90° bend, and ii) a pair of distal slots, each of said distal slots intersecting a respective one of said approximately 90° bends.

2. An insulator according to claim 1, wherein:

said substantially cylindrical member has anti-rotational means for preventing said substantially cylindrical member from rotating in a clevis.

3. An insulator according to claim 2, wherein:

said anti-rotational means comprises a pair of radial surface protrusions which are diametrically opposed to each other.

4. An insulator according to claim 3, wherein:

each of said protrusions has two substantially parallel sides and a proximal curved side.

5. An insulator according to claim 1, wherein:

a proximal portion of each of said longitudinal channels is radially open to the surface of said substantially cylindrical member.

6. An insulator according to claim 3, wherein:

a proximal portion of each of said longitudinal channels is radially open to the surface of said substantially cylindrical member.

7. An insulator according to claim 1, wherein:

said substantially cylindrical member is a unitary ceramic piece.

8. An insulator according to claim 3, wherein:

said substantially cylindrical member is a unitary ceramic piece.

9. An insulator according to claim 5, wherein:

said substantially cylindrical member is a unitary ceramic piece.

10. An insulator according to claim 1, wherein:

said substantially cylindrical member is formed from two substantially identical ceramic pieces.

11. An insulator according to claim 3, wherein:

said substantially cylindrical member is formed from two substantially identical ceramic pieces.

12. An insulator according to claim 5, wherein:

said substantially cylindrical member is formed from two substantially identical ceramic pieces.

13. An insulator for use in combination with a bipolar push rod assembly in a bipolar endoscopic instrument where the bipolar push rod assembly has a pair of conductive rods with each of the rods having a bent distal end for connection to a respective link member, said insulator comprising:

I) a pair of longitudinal channels for receiving said conductive rods, [and]

ii) a pair of distal slots for receiving said link members, each of said slots intersecting a respective longitudinal channel, at least a portion of each slot being defined by opposing wall portions for housing at least a portion of said link members and wherein each of said longitudinal channels terminates in a bend to retain the bent distal ends of the conducting rods and provide for reciprocating movement of said insulator within said push rod assembly upon reciprocation of said conductive rods.

14. An insulator according to claim 13, wherein:

the bend of each channel is approximately 90° and the distal ends of the rods are bent approximately 90°.

15. An insulator according to claim 13, including:

means for preventing said insulator from rotating in a clevis.

16. An insulator according to claim 15, wherein:

said preventing means includes a pair of radial surface protrusions which are diametrically opposed to each other.

17. An insulator according to claim 16, wherein:

each of said protrusions has two substantially parallel sides and a proximal curved side.

18. An insulator according to claim 13, wherein:

a proximal portion of each of said longitudinal channels is radially open to a surface of the insulator.

19. An insulator according to claim 13, wherein:

said insulator is formed as a unitary ceramic piece.

20. An insulator according to claim 13, wherein:

said insulator is formed from two substantially identical ceramic pieces.

* * * * *

UNITED STATES PATENT AND TRADEMARK OFFICE
CERTIFICATE OF CORRECTION

PATENT NO.: 5,846,240

DATED: December 8, 1998

INVENTOR(S): Juergen A. KORTENBACH et al.

It is certified that error appears in the above-identified patent and that said Letters Patent is hereby corrected as shown below:

On the title page, ref. [63], delete ", and Ser. No. 284,793, Aug. 2, 1994, Pat. No. 5,569,243";

In claim 13, column 10, line 8, replace "I)" with --i)--; and

In claim 13, column 10, line 9, delete "[and]".

Signed and Sealed this

Tenth Day of August, 1999

Attest:

Q. TODD DICKINSON

Attesting Officer

Acting Commissioner of Patents and Trademarks